(12) United States Patent
Shushunov

(10) Patent No.: US 12,076,293 B2
(45) Date of Patent: Sep. 3, 2024

(54) CARDIOPULMONARY RESUSCITATION (CPR) USING CHEST COMPRESSIONS SYNCHRONISED WITH ALTERNATING PRESSURE MECHANICAL VENTILATION

(71) Applicant: Sergey Shushunov, Buffalo Grove, IL (US)

(72) Inventor: Sergey Shushunov, Buffalo Grove, IL (US)

( * ) Notice: Subject to any disclaimer, the term of this patent is extended or adjusted under 35 U.S.C. 154(b) by 582 days.

(21) Appl. No.: 17/307,089

(22) Filed: May 4, 2021

(65) Prior Publication Data

US 2022/0008288 A1 Jan. 13, 2022

Related U.S. Application Data

(60) Provisional application No. 63/050,190, filed on Jul. 10, 2020.

(51) Int. Cl.
*A61H 31/00* (2006.01)
*A61M 16/00* (2006.01)
(Continued)

(52) U.S. Cl.
CPC ....... *A61H 31/007* (2013.01); *A61M 16/0075* (2013.01); *A61M 16/20* (2013.01);
(Continued)

(58) Field of Classification Search
CPC ................ A61H 31/007; A61H 31/005; A61H 2201/1619; A61H 31/00; A61H 2201/10; A61H 2201/1238; A61H 31/006; A61H 2201/107; A61H 31/004; A61H 2031/001; A61H 2031/002; A61M 16/0833; A61M 16/022; A61M 2205/581; A61M 2202/0208; A61M 2202/0225;
(Continued)

(56) References Cited

U.S. PATENT DOCUMENTS 1,197,232 A 9/1916 Pierpont
3,106,204 A * 10/1963 Paramelle ......... A61M 16/0075
128/205.24

(Continued)

OTHER PUBLICATIONS

Aufderheide, T.P. et al.; "A Trial of an Impedance Threshold Device in Out-of-Hospital Cardiac Arrest"; N Engl J Med. Sep. 1, 2011; 365(9).

(Continued)

*Primary Examiner* — Tu A Vo
(74) *Attorney, Agent, or Firm* — Thomas E. Lees, LLC

(57) ABSTRACT

Disclosed are systems and processes related to cardiopulmonary resuscitation (CPR). One embodiment of the system comprises an inspiration chamber and an expiration chamber, which work cooperatively to provide gas (e.g., Oxygen ($O_2$)) to a subject (e.g., human patient) during inspiration and extract and expel expired gas (e.g., Carbon Dioxide ($CO_2$)) from the subject during expiration as a medical professional applies CPR to the subject. In other words, this disclosure provides systems and processes that allow for substantially synchronous chest compressions with positive pressure active inspirations and, also, substantially synchronous chest decompressions with negative pressure active expirations.

15 Claims, 6 Drawing Sheets

(51) Int. Cl.
*A61M 16/08* (2006.01)
*A61M 16/20* (2006.01)

(52) U.S. Cl.
CPC .......... *A61H 31/005* (2013.01); *A61H 31/006* (2013.01); *A61H 2201/107* (2013.01); *A61H 2201/1238* (2013.01); *A61H 2201/1619* (2013.01); *A61M 16/0833* (2014.02); *A61M 16/208* (2013.01); *A61M 16/209* (2014.02); *A61M 2202/0208* (2013.01); *A61M 2205/05* (2013.01); *A61M 2205/071* (2013.01); *A61M 2205/581* (2013.01); *A61M 2205/583* (2013.01); *A61M 2230/04* (2013.01); *A61M 2230/65* (2013.01)

(58) Field of Classification Search
CPC ........ A61M 2205/05; A61M 2205/071; A61M 2230/04; A61M 2230/205; A61M 2230/65; A61M 2202/0007; A61M 2202/0014; A61M 16/0057; A61M 16/0075–0084; A61M 16/208–209
See application file for complete search history.

(56) References Cited

U.S. PATENT DOCUMENTS

| | | | |
|---|---|---|---|
| 3,336,920 A * | 8/1967 | Thomas | A61H 31/006 601/106 |
| 3,461,866 A | 8/1969 | Ritchie | |
| 3,528,414 A * | 9/1970 | Schueller | A61H 31/006 128/202.11 |
| 3,918,447 A | 11/1975 | Inkster et al. | |
| 4,237,872 A * | 12/1980 | Harrigan | A61H 31/007 601/1 |
| 4,349,015 A * | 9/1982 | Alferness | A61H 9/0078 128/205.16 |
| 4,782,831 A | 12/1988 | Gallant | |
| 4,870,962 A | 10/1989 | Sitnik | |
| 4,934,360 A * | 6/1990 | Heilbron | A61M 16/0075 128/205.16 |
| 5,313,938 A * | 5/1994 | Garfield | A61M 1/684 128/205.24 |
| 5,628,305 A | 5/1997 | Melker | |
| 5,692,498 A * | 12/1997 | Lurie | A61M 16/20 128/205.24 |
| 6,604,523 B2 | 8/2003 | Lurie et al. | |
| 6,988,499 B2 * | 1/2006 | Holt | A61M 16/0075 128/205.16 |
| 7,766,011 B2 | 8/2010 | Lurie | |
| 8,105,249 B2 | 1/2012 | Freeman | |
| 10,201,474 B2 | 2/2019 | Belalcazar | |
| 10,251,811 B2 | 4/2019 | Freeman | |
| 10,512,749 B2 | 12/2019 | Lurie et al. | |
| 2006/0180146 A1 * | 8/2006 | Thompson | A61M 16/10 128/202.28 |
| 2007/0225623 A1 * | 9/2007 | Freeman | A61M 16/1075 601/44 |
| 2015/0224022 A1 * | 8/2015 | Hanson | A61H 31/005 601/41 |
| 2018/0154094 A1 * | 6/2018 | Jacquot | A61M 16/0051 |
| 2019/0262226 A1 | 8/2019 | Freeman | |

OTHER PUBLICATIONS

Convertino V.A. et al.; "Optimizing the Respiratory Pump: Harnessing Inspiratory Resistance to Treat Systemic Hypotension"; Respiratory Care; Jun. 2011; vol. 56 No. 6.

Kill, C. et al.; "Chest Compression Synchronized Ventilation versus Intermitted Positive Pressure Ventilation during Cardiopulmonary Resuscitation in a Pig Model"; PLoS One 10(5); May 26, 2015.

* cited by examiner

CARDIOPULMONARY RESUSCITATION (CPR) USING CHEST COMPRESSIONS SYNCHRONISED WITH ALTERNATING PRESSURE MECHANICAL VENTILATION

CROSS REFERENCE TO RELATED APPLICATIONS

This application claims the benefit of U.S. Provisional Patent Application Ser. No. 63/050,190, filed Jul. 10, 2020, having the title "CARDIOPULMONARY RESUSCITATION (CPR)," the disclosure of which is hereby incorporated by reference.

BACKGROUND

Field of the Disclosure

The present disclosure relates generally to medical systems and processes; more particularly, to systems, devices, and processes relating to cardiopulmonary resuscitation (CPR).

Description of Related Art

Cardiopulmonary resuscitation (CPR) is typically performed on subjects (e.g., human patients) in cardiac arrest in an effort to return spontaneous circulation in the subject. In general, there are two forms of CPR. A typical bystander/rescuer may administer chest compressions only. Healthcare providers that administer CPR may use a combination of chest compressions followed by forced ventilation (such as mouth to mouth breathing). Because of the importance of CPR, improved systems, processes, or techniques relating to CPR are desired by the medical community.

SUMMARY

The present disclosure relates to cardiopulmonary resuscitation (CPR). Briefly described, aspects herein comprise a system and/or device, e.g., implemented as a ventilator device, which is used in the application of CPR where ventilation is applied in synchrony with chest compressions and decompressions. For instance, in an example embodiment, a device includes an inspiration chamber and an expiration chamber, which work cooperatively to provide gas exchange by delivering Oxygen ($O_2$) or air to a subject (e.g., human patient) during inspiration and extracting and expelling expired Carbon Dioxide ($CO_2$) gas from the subject during expiration as a care giver applies CPR to the subject. In other words, the device allows for substantially synchronous chest compressions with positive pressure actively induced inspirations and, also, substantially synchronous chest decompressions with negative pressure active expirations.

In some embodiments, a system and/or device can comprise an adjustable inspiratory chamber pressure release valve. For instance, in an example embodiment, the adjustable pressure release valve can be set to a pressure of approximately 30 cm $H_2O$ up to approximately 300 cm $H_2O$.

In some embodiments, a system and/or device can also and/or alternatively comprise an expiratory chamber vacuum release valve. For instance, in an example embodiment, the vacuum release valve can be adjustable from approximately 0 to approximately −50 cm $H_2O$.

In yet further embodiments, a system and/or device can also and/or alternatively produce relatively high pressure. Here, the high pressure produced by inspiration/chest compression allows standardizing chest compressions and maximizing left ventricular stroke volume generated by every chest compression regardless of the chest wall anatomy or the depth of chest compression.

Other embodiments provide processes of administering CPR, comprising applying ventilation in synchrony with chest compressions and decompressions. By way of example, a process herein comprises applying substantially synchronous chest compressions with positive pressure active inspirations and, applying substantially synchronous chest decompressions with negative pressure active expirations. For instance, the process may be carried out by the above system.

Other processes can include adjusting, e.g., via an adjustable inspiratory pressure release valve, a pressure, e.g., from approximately 30 cm $H_2O$ up to approximately 300 cm $H_2O$; adjusting, e.g., via an expiratory vacuum release valve, a vacuum from approximately 0 to approximately −50 cm $H_2O$; producing relatively high pressure, e.g., producing high pressure by inspiration/chest compression so as to allow for standardizing intrathoracic pressure and maximizing stroke volume generated by every chest compression regardless of the chest wall anatomy or the depth of chest compression; or combinations thereof.

Other systems, devices, processes, features, and advantages will be or become apparent to one with skill in the art upon examination of the following drawings and detailed description. It is intended that all such additional systems, processes, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1:
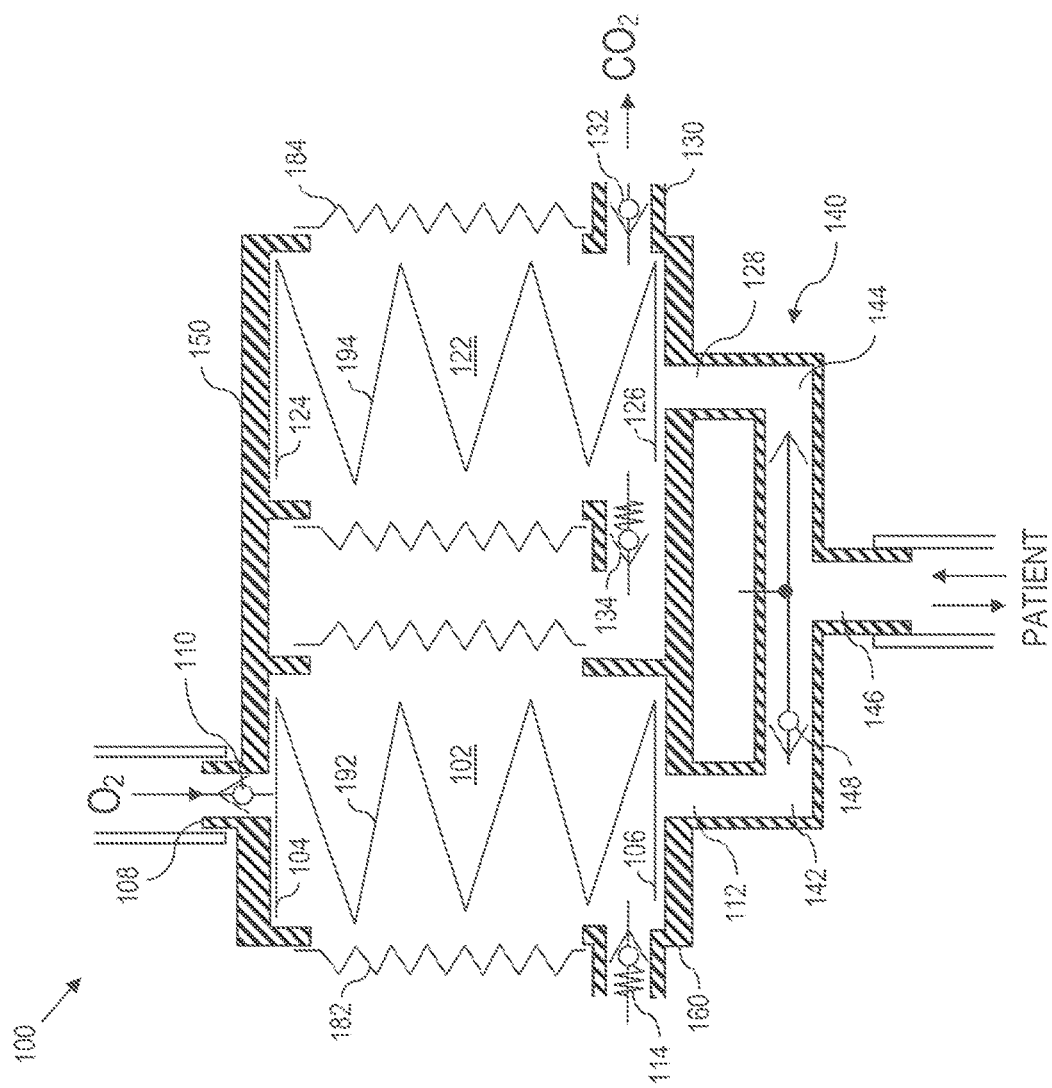
FIG. 1 is a diagram showing an embodiment of a ventilation system comprising an inspiration chamber and an expiration chamber.

Cardiopulmonary resuscitation (CPR) is an emergency procedure that is typically performed for people in cardiac arrest to achieve the return of spontaneous circulation by administering chest compressions and artificial ventilation. Some studies have determined that an optimal rate of chest compressions is approximately one hundred (~100) compressions per minute and the rate of artificial breaths is approximately two (~2) for every thirty (30) chest compressions. As is known, the purpose of CPR is to partially restore blood flow to the brain and to the heart.

In the United States the survival rate following CPR for out-of-hospital cardiac arrest has been reported at approximately ten percent (~10%) and depends largely on the quality of CPR (because the quality of CPR correlates to amount of cardiac output). Under substantially normal conditions, stroke volume generated by the heart depends on the force of the contraction of the heart and the volume of the blood filling the chambers of the heart. During traditional CPR, the stroke volume depends on the effectiveness of chest compressions, while the volume of blood filling heart chambers is somewhat uncontrollable. The stroke volume generated by chest compressions depends on several factors, including but not limited to: chest anatomy; body mass of the person receiving CPR; body mass of the person administering CPR; the strength of the person administering CPR; etc.

Good quality chest compressions achieve a systolic blood pressure of approximately ninety (~90) to approximately one hundred (~100) millimeters of mercury (mmHg) or approximately one-hundred-and-twenty (~120) to approximately one-hundred-and-forty (~140) centimeters of water ($cmH_2O$). However, the cardiac output generated by the traditional CPR is usually between approximately twenty-five percent (~25%) to approximately thirty percent (~30%) of normal cardiac output, which is often insufficient to preserve good cerebral and myocardial blood flow and to produce good resuscitation outcomes.

During CPR, one recommendation is to administer two (2) artificial breaths for every thirty (30) chest compressions using a traditional resuscitation ventilation Bag Valve Mask (BVM) device. Normally, a BVM device has a single chamber made from silicone rubber, which when compressed generates pressure up to ~60 $cmH_2O$ to inflate the lungs for adults and up to ~30 $cmH_2O$ for ventilating infants and children. When decompressed, the BVM allows lungs to passively deflate due to atmospheric pressure. Some have shown that compression and decompression of BVM influences stroke volume as a function of the synchronicity (or lack thereof) between chest compressions and BVM compressions.

One of the problems occurring during chest compression CPR is air trapping, which can result in increased intrathoracic pressure during the decompression phase, which decreases a pressure gradient between venous circulation and the right atrium, thereby limiting blood return to the heart and worsening the CPR quality. The cardiac output and vital organ perfusion can be improved by the administration of artificial breaths in synchrony with chest compressions, which results in the consistently higher elevation of intrathoracic pressure, with each chest compression/bag inflation. Some studies have shown that the cardiac output and vital organ perfusion can be improved by applying a negative intrathoracic pressure during decompression of the chest, using, for example, an Impedance Threshold Device (ITD) which works by blocking airflow through an endotracheal tube into the lungs during the chest decompression. It is believed that negative intrathoracic pressure during the decompression phase of the CPR improves blood return to the heart and increases heart stroke volume vital to organ perfusion pressure. However, some studies show that the use of ITD does not produce better outcomes in clinical trials, with a possible explanation being the inability of ITD to improve the acid-base balance during CPR, which suggest that there is an impediment to gas exchange using ITD.

To mitigate some of these effects, aspects of this disclosure provide systems, devices, and processes, which permit chest compressions, which can be combined with substantially synchronous positive pressure inspirations. In some embodiments, the positive pressure inspirations are actively induced inspirations (e.g., mechanically induced inspirations). Correspondingly, aspects of this disclosure provide systems, devices, and processes, which permit positive pressure inspirations, which can be combined with substantially synchronous chest compressions. Again, in some embodiments, the positive pressure inspirations are actively induced inspirations (e.g., administered actively by a rescuer).

Aspects herein also provide systems, devices, and processes, which permit chest decompressions, which can be combined with substantially synchronous negative pressure expirations. In some embodiments, the negative pressure expirations are actively induced exhalations. Correspondingly, aspects of this disclosure provide systems, devices, and processes, which permit negative pressure expirations, which can be combined with substantially synchronous chest decompressions. Again, in some embodiments, the negative pressure expirations are actively induced exhalations.

Yet further embodiments provide systems, devices, and processes, which permit chest compressions combined with substantially synchronous positive pressure active inspirations as well as chest decompressions combined with substantially synchronous negative pressure active expirations (also designated herein as Chest Compression Synchronized Bi-Phasic Ventilation (CCSBV)). In example embodiments, the CCSBV permits a one-to-one (1:1) correspondence between breaths and chest compressions, thereby augmenting stroke volumes produced by chest compressions while concurrently generating negative intrathoracic pressure during the decompression phase of CPR to increase blood return to the heart and will increase the filling volume of the heart chambers.

Briefly described, an embodiment of the system comprises an inspiration chamber and an expiration chamber, which work cooperatively to provide gas (e.g., Oxygen ($O_2$)) to a subject (e.g., human patient or other mammalian species on which CPR can be performed) during inspiration and extract and expel expired gas (e.g., Carbon Dioxide ($CO_2$)) from the subject during expiration as a medical professional applies CPR to the subject.

Aspects herein provide devices, systems and processes that improve venous return to the heart without impeding lung ventilation and gas exchange. For instance, a ventilator system as set out herein can prevent the development of air trapping in the airways by applying low negative pressure during active expiration. As a result of improved quality of chest compressions, increased blood return, and avoidance of air trapping, the device and/or process herein will improve stroke volume, cardiac output, and vital organs perfusion. According to some embodiments herein, a system and/or device as set out herein is manually operated by a user. In other embodiments, a system and/or device as set out herein is mechanical/automated. In yet further embodiments, a system and/or device as set out herein may be manually operated or automatically operated. Yet further, a ventilator device herein can be incorporated into a manual chest compression device, thereby forming a system of components. As such, a ventilator as set out herein can work in synchrony with a mechanical chest compression device.

As will be described in greater detail herein, synchronization of chest compressions and decompressions with lungs inflations and deflations can be achieved by making a single device, which acts as a chest compressor and ventilator at the same time. This device can be manual, or mechanical. Moreover, the device can use pneumatic driving mechanisms, electrical driving mechanisms, etc. Solely by way of example, an illustrative embodiment to implement a method of synchronization of chest compressions and ventilation is having a single device where a ventilator is interpolated or built into a chest compressor.

In other embodiments, synchronization of chest compressions and decompressions with lungs inflations and deflations can be achieved by the synchronization of two independent devices (e.g., a chest compressor and a ventilator (shown as 410 in FIG. 4, below)). Synchronization can be achieved by utilizing a synchronization unit (such as the one shown as 420 in FIG. 4, below) to initiate chest compressions and lung inflations and chest decompressions and lung deflations at substantially the same time.

Yet further, in additional embodiments, synchronization of chest compressions and decompressions with lungs inflations and deflations can be achieved by manual synchronization, e.g., by one provider performing chest compressions/decompressions and another provider performing lung inflations and deflations, e.g., using visual or audio signals.

In some embodiments, synchronization can be achieved by detecting the chest impedance changes during compressions/decompressions and using these changes as signals for the ventilator.

In this manner, the ventilator is used in synchrony with chest compressions and decompressions, e.g., via the chest compressor. Regardless, chest compression is synchronized with lung inflation, and chest decompression is synchronized with lung deflation. As noted more fully herein, embodiments of the ventilator can have an inflation pressure release valve adjustable from approximately 30 cm $H_2O$ to approximately 300 cm $H_2O$. Also, the ventilator can have a deflation vacuum release valve adjustable from approximately 0 to approximately −50 cm $H_2O$. However, the magnitude of inflation and deflation pressure can be adjusted to optimize/maximize stroke volume/cardiac output. Having provided a broad technical solution to a technical problem, reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

FIG. 1 is a diagram showing an embodiment of a system 100 (or a ventilation system) comprising an inspiration chamber and an expiration chamber. For purposes of clarity, the individual components of the system 100 are described in detail and, thereafter, the operation of the system 100 is explained with reference to the described components.

With this in mind, in the embodiment of FIG. 1, the system 100 comprises a selectively compressible and expandable inspiration chamber 102. The inspiration chamber comprises an inspiration chamber top 104 and an inspiration chamber bottom 106, which (in combination) partially define the space in the inspiration chamber 102.

The inspiration chamber 102 further comprises an inspiration chamber inlet 108 for receiving gas (e.g., Oxygen ($O_2$), air, etc.). Preferably, the inspiration chamber 102 receives the gas when pressure in the inspiration chamber 102 is lower than atmospheric pressure. However, the system 100 can also be configured to accommodate pressures that deviate from atmospheric pressure. The inspiration chamber 102 further comprises an inspiration chamber inlet valve 110 that is operatively coupled to the inspiration chamber inlet 108. The inspiration chamber inlet valve 110 opens when the pressure in the inspiration chamber 102 is lower than the atmospheric pressure (or other predefined threshold pressure) and, furthermore, closes when the pressure in the inspiration chamber 102 is higher than the atmospheric pressure (or other predefined threshold pressure).

The inspiration chamber 102 further comprises an inspiration chamber outlet 112 for expelling the gas (e.g., Oxygen, air, etc.) from the inspiration chamber 102 when the pressure in the inspiration chamber 102 is higher than the atmospheric pressure (or other predefined threshold pressure). This expelled gas (e.g., Oxygen, air, etc.) is what the subject or patient eventually receives. It should be appreciated that, for some embodiments, the gas that is provided to the patient can be hyper-cold air other gas at sub-zero temperatures that are suitable for use in targeted temperature management systems, such as in therapeutic hypothermia.

For some embodiments, the inspiration chamber 102 further comprises an inspiration chamber pressure release valve 114 that opens when pressure inside of the inspiration chamber 102 is higher than a predefined threshold for a maximum positive pressure. The inspiration chamber pressure release valve 114 limits the force applied by the air to the lungs of the patient, thereby providing a safety mechanism that protects the lungs. For example, if the human patient is a child or an infant, then the predefined threshold positive pressure is from approximately thirty centimeters of water (~30 $cmH_2O$). However, for adult patients, the predefined maximum positive pressure can be set from approximately sixty centimeters of water (~60 $cmH_2O$). Because the system 100 can have some pliability, it is also possible to set the predefined maximum positive pressure at approximately one-hundred centimeters of water (~100 $cmH_2O$) or, in some cases, as high as approximately one-hundred-and-forty centimeters of water (~140 $cmH_2O$). It should be noted that those having ordinary skill in the art have suggested such high positive pressures (e.g., ~140 $cmH_2O$) to be dangerous as applying too much pressure in the lungs. However, contrary to this conventional wisdom, some embodiments of the CCSBV (as described in greater detail, below) should permit such high positive pressures because concurrent chest compression applies intrathoracic pressure that counterbalances the pressure within the lungs and limiting lung inflation volume, thereby allowing for much higher pressures within the lung than what conventional wisdom teaches.

Continuing with FIG. 1, the system 100 also comprises a selectively compressible and expandable expiration chamber 122, which is operatively coupled to the inspiration chamber 102. The expiration chamber 122 comprises an expiration chamber top 124 that is substantially aligned with the inspiration chamber top 104. The expiration chamber 122 further comprises an expiration chamber bottom 126, which is substantially aligned with the inspiration chamber bottom 106. The alignment of the inspiration chamber top 104 with the expiration chamber top 124 and the alignment of the inspiration chamber bottom 106 with the expiration chamber bottom 126 allow for substantially concurrent compression and expansion of the inspiration chamber 102 with the expiration chamber 122.

The expiration chamber 122 also comprises an expiration chamber inlet 128 for receiving expired gas (e.g., Carbon Dioxide ($CO_2$) from the subject or patient). For some embodiments, the expired gas is received in the expiration chamber 122 when pressure in the expiration chamber 122 is lower than the atmospheric pressure. However, for other embodiments, the functional pressure in the expiration chamber 122 can deviate upward or downward from atmospheric pressure as the needs of the subject (or patient) change. As explained in detail later, the expiration chamber 122 provides a suction force that actively pulls or draws expired gas (e.g., $CO_2$) from the lungs of a subject or patient, rather than allowing the expired gas to passively exit the lungs.

The expiration chamber 122 further comprises an expiration chamber outlet 130 for expelling the expired gas (e.g., $CO_2$) from the expiration chamber 122. Again, for some embodiments, the expired gas is expelled when the pressure in the expiration chamber 122 is higher than a predefined threshold pressure (e.g., atmospheric pressure). Consequently, for some embodiments, the expiration chamber 122 also comprises an expiration chamber outlet valve 132, which is operatively coupled to the expiration chamber outlet 130. The expiration chamber valve 132 opens when the pressure in the expiration chamber 122 is higher than the predefined threshold pressure (e.g., atmospheric pressure) and closes when the pressure in the expiration chamber 122 is lower than the predefined threshold pressure (e.g., atmospheric pressure or some other suitable pressure limit).

Similar to the inspiration chamber 102, the expiration chamber 122 has an expiration chamber pressure release valve 134, which opens when the pressure in the expiration chamber 122 is lower than a predefined threshold maximum negative pressure. In other words, the expiration chamber pressure release valve 134 prevents too much negative pressure (or suction) from being applied to the lungs when pulling or drawing the expired air (e.g., $CO_2$) from the lungs.

Continuing with FIG. 1, the system 100 further comprises a spring-loaded shuttle valve 140 with an inspiration conduit 142 that is mechanically coupled to the inspiration chamber outlet 112, an expiration conduit 144 that is mechanically coupled to the expiration chamber inlet 128, and a subject conduit 146 (located between the inspiration conduit 142 and the expiration conduit 144) that selectively supplies the gas to the subject and receives from the patient the expired gas (e.g., $CO_2$). The subject conduit 146, for some embodiments, is attached to a tracheal tube (not shown in FIG. 1), such as the one shown in FIGS. 3A and 3B, below.

The spring-loaded shuttle valve 140 comprises a spring-loaded shuttle 148 with a default position that closes the inspiration conduit 142 and opens the expiration conduit 144 in the absence of pressure being applied to the spring-loaded shuttle 148. The spring-loaded shuttle 148 selectively opens the inspiration conduit 142 and closes the expiration conduit 144 when positive pressure from the inspiration chamber 102 is applied to the spring-loaded shuttle 148. Conversely, the spring-loaded shuttle 148 closes the inspiration conduit 142 and opens the expiration conduit 144 when no positive pressure is applied from the inspiration chamber 102 to the spring-loaded shuttle 148. Based on this mechanism, the spring-loaded shuttle valve 140 allows either the inspiration chamber 102 to force gas (e.g., $O_2$ or air) into the lungs or, in the alternative, the expiration chamber 122 to force expired gas (e.g., $CO_2$) from the lungs through negative pressure (or suction). It should be appreciated that, for some embodiments, an electromechanical valve is used instead of a spring-loaded shuttle valve 140.

As shown in FIG. 1, the system 100 further comprises a substantially rigid top 150 and a substantially rigid bottom 160. The substantially rigid top 150 is mechanically coupled to the inspiration chamber top 104 and the expiration chamber top 124, while the substantially rigid bottom 160 is mechanically coupled to the inspiration chamber bottom 106 and the expiration chamber bottom 126. The substantially rigid top 150 and the substantially rigid bottom 160 work in cooperation to concurrently compress both the inspiration chamber 102 and the expiration chamber 122. The concurrent compression forces the gas (e.g., air) from the inspiration chamber 102 into the lungs while at the same time expelling any previously expired gas (e.g., $CO_2$) from the expiration chamber 122.

Of course, insofar as both chambers 102, 122 are compressible, it should be appreciated that the system also comprises expanding means for concurrently expanding both the chambers 102, 122 after they have been compressed. Preferably, the expanding means expands both the inspiration chamber 102 and the expiration chamber 122 at substantially the same time and, also, to substantially their respective pre-compression states within a predefined rebound time (e.g., approximately three hundred milliseconds (~300 ms)).

In the system 100 of FIG. 1, an embodiment of the expanding means comprises a deformable wall 182 on the inspiration chamber 102 and a deformable wall 184 on the expiration chamber 122. In the illustrated example embodiment, the deformable walls 182, 184, located between the substantially rigid top 150 and the substantially rigid bottom 160 and have a default shape prior to the compression of the two (2) chambers 102, 122. Other configurations may be implemented within the present disclosure. Because the deformable walls 182, 184 have physical properties that allow them to return to their respective default shapes, for some embodiments, the deformable walls 182, 184 have predefined stiffnesses. As such, the deformable walls 182, 184 deform concurrently with the compression of the inspiration chamber 102 and the expiration chamber 122 and return concurrently to their default shapes, thereby expanding the inspiration chamber 102 and the expiration chamber 122.

In an alternative embodiment of the system 100, the expanding means comprises one or more compressible springs 192, 194 located between the substantially rigid top 150 and the substantially rigid bottom 160. It should be appreciated that, in some embodiments a compressible spring 192 is located in the inspiration chamber 102, while in other embodiments a compressible spring 194 is located in the expiration chamber 122, while in yet other embodiments compressible springs 192, 194 can be located in both the inspiration chamber 102 and the expiration chamber 122. Alternatively, the compressible spring(s) 192, 194 can be located in a suitable space between the inspiration chamber 102 and the expiration chamber 122. Preferably, the compressible spring 192, 194 has a spring constant. Thus, when the spring 192, 194 is compressed during the compression of the inspiration chamber 102 and the expiration chamber 122, the spring 192, 194 has a tendency to return to its pre-compression load within a predefined rebound time after being compressed (e.g., ~300 ms or other appropriate rebound time that can be applied through alteration of the spring constant).

Figure 2:
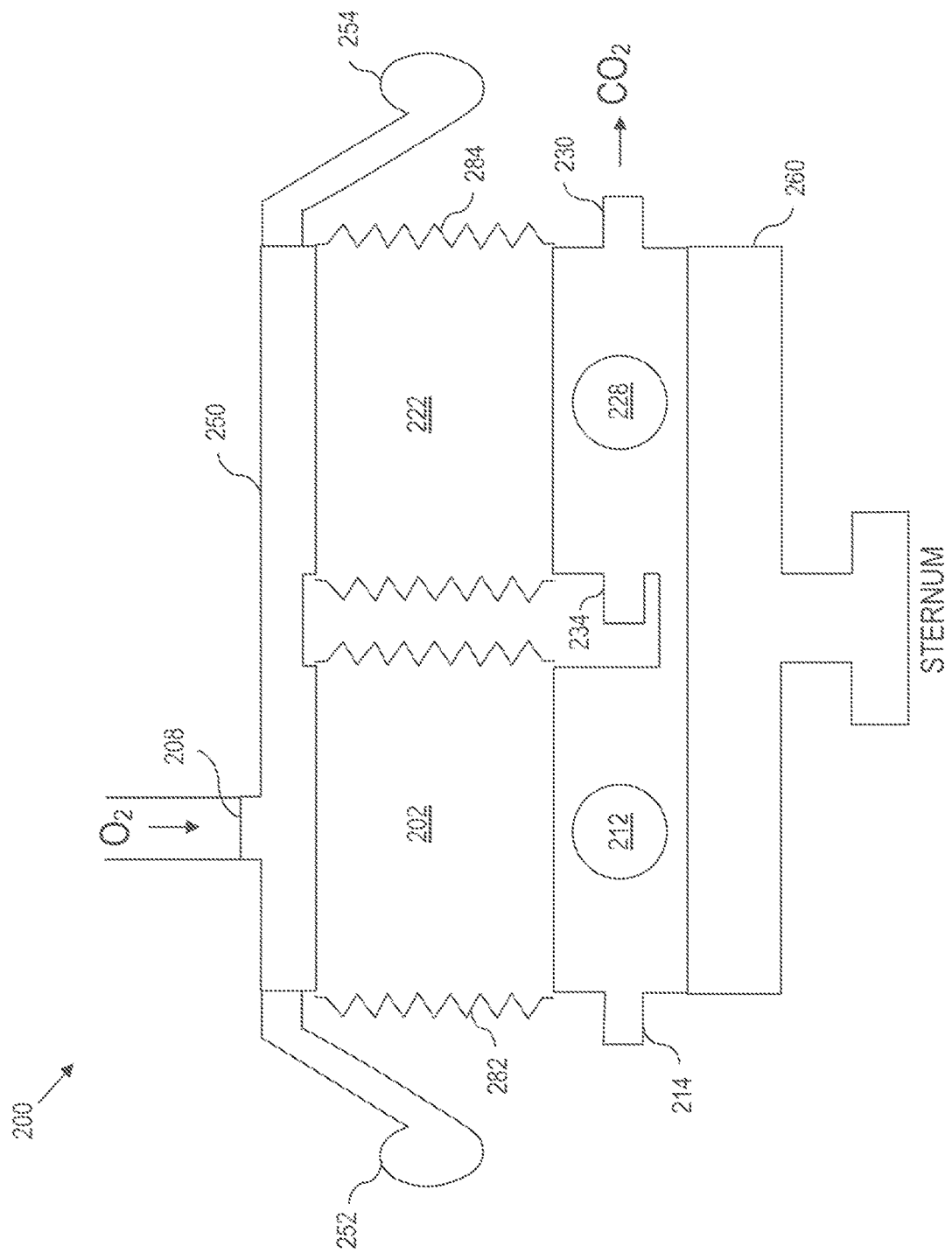
FIG. 2 is a diagram showing an embodiment of a ventilation system that permits substantially concurrent chest compression with ventilation.

Turning now to FIG. 2, shown in FIG. 2 is another embodiment of a system 200 that permits substantially concurrent chest compression with ventilation. Insofar as similar components are described in detail with reference to FIG. 1, only a truncated description of corresponding components is provided with reference to FIG. 2.

As shown in FIG. 2, the system 200 comprises an inspiration chamber 202. The inspiration chamber 202 comprises an inspiration inlet 208 (for receiving gas, such as $O_2$, air, etc.), an inspiration outlet 212 (for supplying the gas (e.g., $O_2$, air, etc.) to a patient, and an inspiration chamber pressure release valve 214 (for limiting the positive pressure within the inspiration chamber 202).

The system 200 also comprises an expiration chamber 222. The expiration chamber 222 comprises an expiration chamber inlet 228 (for receiving expired gas (e.g., $CO_2$) from the patient), an expiration chamber outlet 230 (for expelling the expired gas (e.g., $CO_2$) from the expiration chamber 222), and an expiration chamber pressure release valve 234 (for limiting the negative pressure in the expiration chamber 222).

The system 200 also comprises a substantially rigid top 250, which includes handles 252, 254. In the embodiment of FIG. 2, the system 200 comprises a left handle 252 and a right handle 254, both of which can be used by a person administering CPR apply compression forces to the system 200. As shown in FIG. 2, the system 200 also comprises a substantially rigid bottom 260 for contacting a sternum (or similar anatomical location) in a patient. Thus, the substantially rigid bottom 260 works in cooperation with the substantially rigid top 250 to compress both the inspiration chamber 202 and the expiration chamber 222 and, substantially concurrently, apply chest compression to a patient. Thus, the system 200 concurrently forces the gas (e.g., $O_2$, air, etc.) from the inspiration chamber 102 into the lungs while at the same time expelling any previously expired gas (e.g., $CO_2$) from the expiration chamber 122. In synchrony with the inspiration and expiration of the gases, the system 200 permits application of chest compressions to the patient.

Similar to FIG. 1, the system 200 also comprises expanding means 282, 284 for concurrently expanding both the chambers 202, 222 after they have been compressed.

It should be appreciated that the application of artificial breaths in synchrony with chest compressions will largely guarantee consistently higher intrathoracic pressures with each chest compression. These higher intrathoracic pressures allow for much higher positive pressures than what conventional wisdom teaches would be safe. As such, although those having ordinary skill in the art have suggested such high positive pressures (e.g., ~140 $cmH_2O$) are dangerous, contrary to this conventional wisdom some embodiments of the CCSBV (as described in greater detail, below) should permit such high positive pressures within the lungs.

Figure 3A:
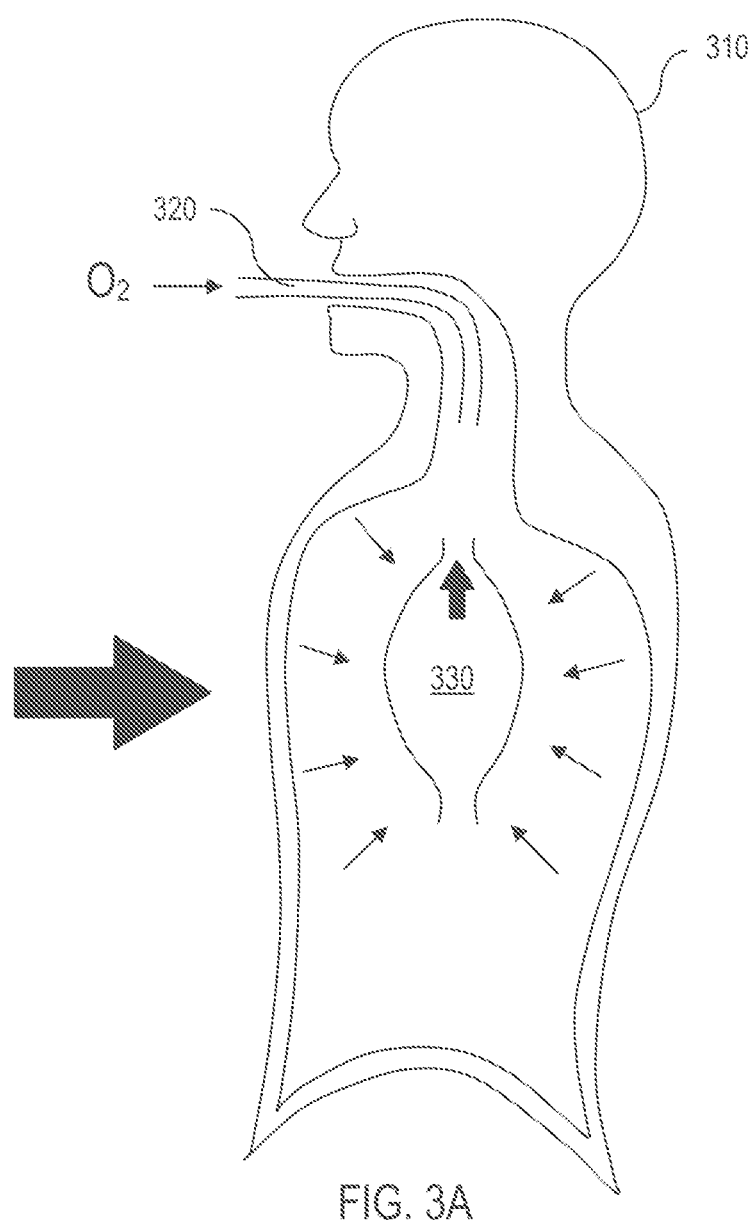
FIG. 3A is a schematic diagram showing substantially concurrent chest compression with inspiration.
Figure 3B:
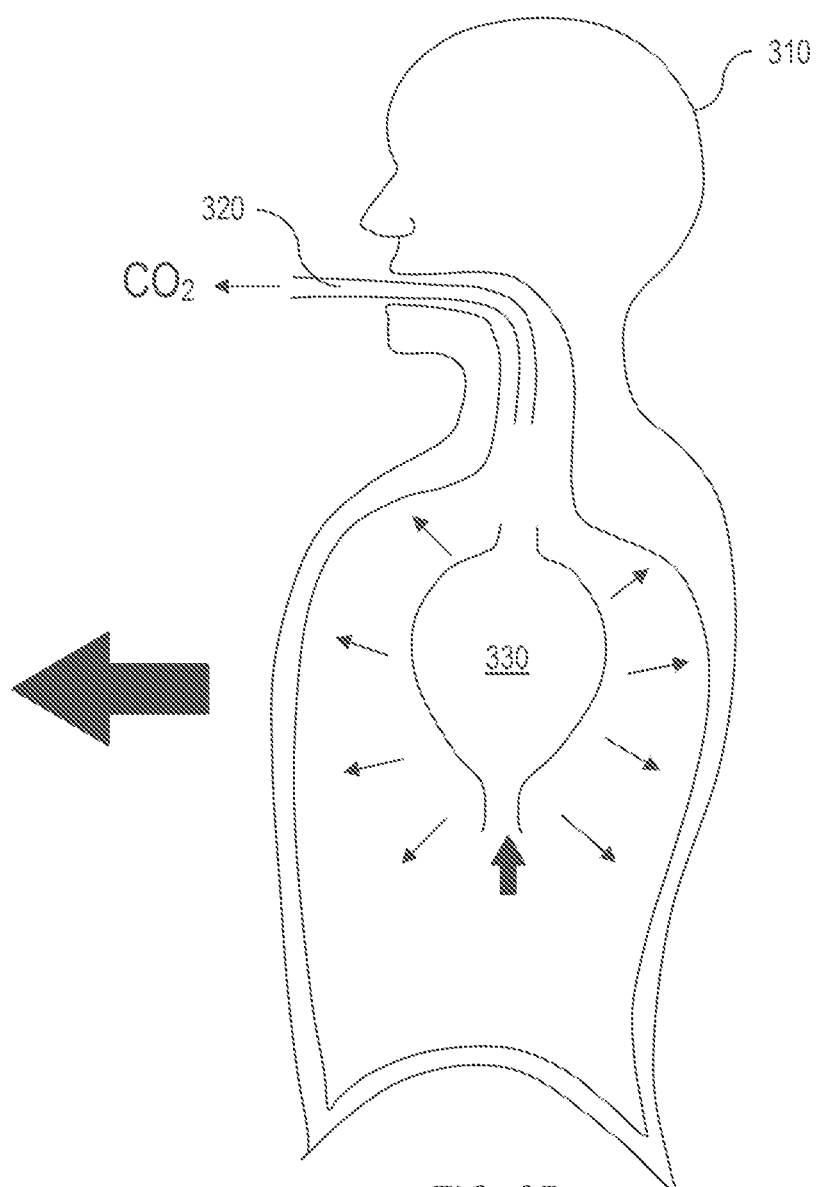
FIG. 3B is a schematic diagram showing substantially concurrent expiration and passive chest expansion.
Figure 4:
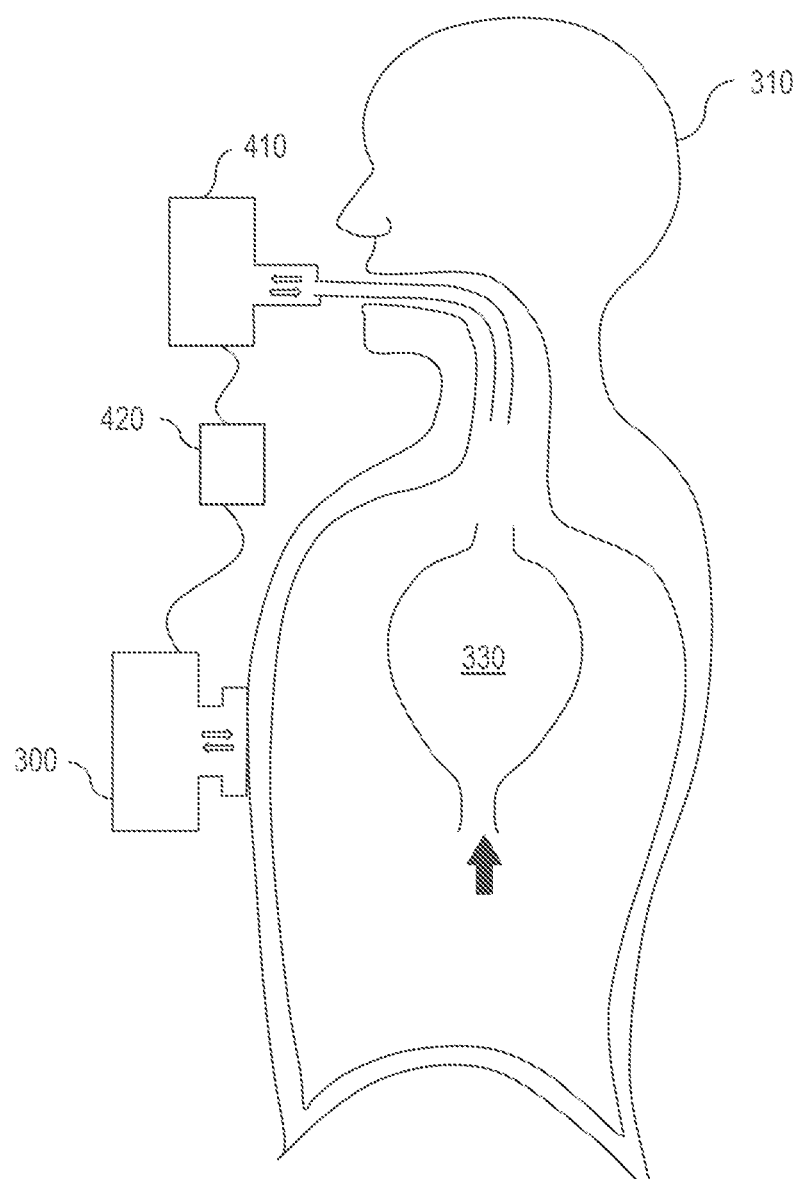
FIG. 4 is a diagram showing an embodiment of a chest compression system, a ventilation system, and a synchronization unit, all of which are applied to a subject.

Turning now to FIGS. 3A, 3B (collectively designated as FIG. 3), and FIG. 4, operation of the system 100 (FIG. 1), 200 (FIG. 2), 300 (FIG. 4) is explained using schematic diagrams of a patient 310. Specifically, FIG. 4 shows the placement of the system 300 with a ventilation system 410 and a synchronization unit 420 on a patient 310, while FIG. 3A shows inspiration of $O_2$ and FIG. 3B show the expiration of $CO_2$.

As shown in FIG. 3A, during compression of the system 100, 200, 300 the inspiration chamber 102 generates positive pressure, thereby forcing gas (e.g., $O_2$, air, etc.) into the airways through an endotracheal tube 320 (or a laryngeal mask airway (not shown) and inflates the lungs. The inflation of the lungs generates positive intrathoracic pressure while the expiration chamber 122 concurrently expels the expired air into the environment. As noted above, the compression and decompression of the chest can be synchronized and mechanically induced with a synchronization unit 420, as shown in FIG. 4.

Figure 5:
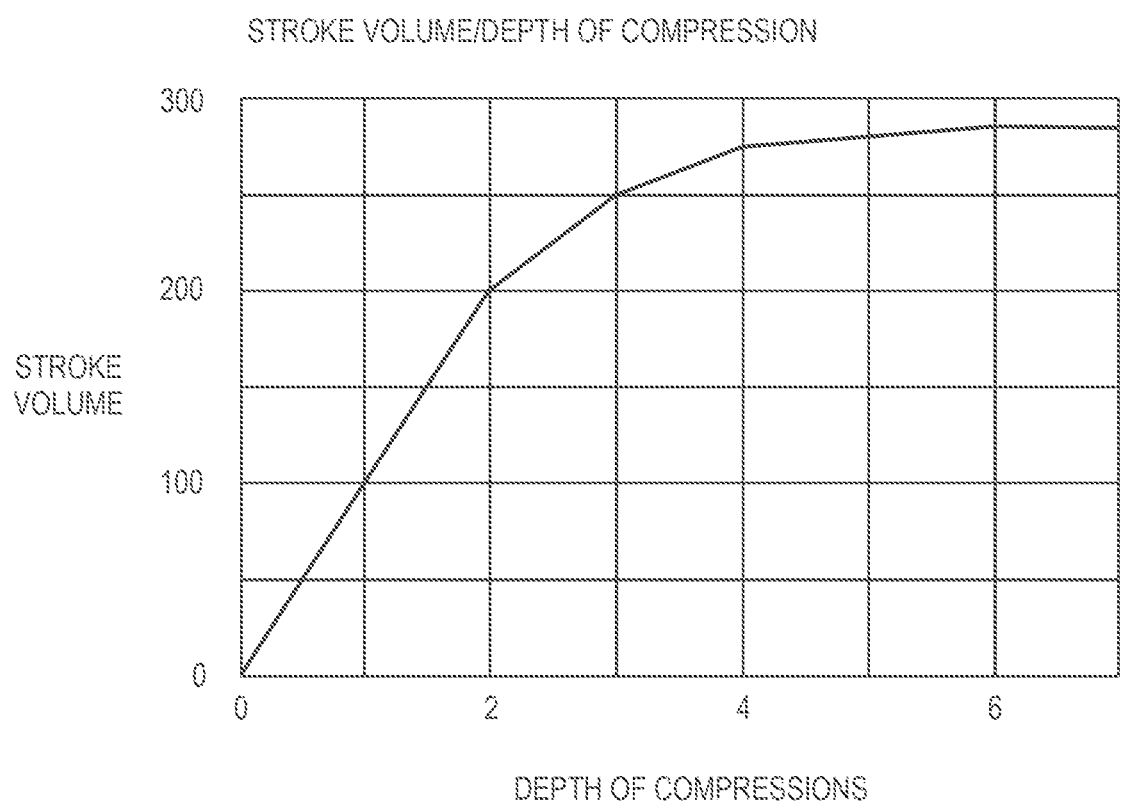
FIG. 5 is a chart showing an example stroke volume (in milliliters (mL)) as a function of depth of compression (in centimeters (cm)).

To be effective, the magnitude of inflating pressure in inspiration chamber 102 should be equal to or higher than systolic pressure of the patient 310 that is generated during chest compressions (for example, up to ~120 $cmH_2O$, if not more). Others have shown that mechanical ventilation in synchrony with chest compressions using an inflation pressure of ~140 $cmH_2O$ is possible. Apparently, even under very high inflation pressures, the lungs should not become overdistended or rupture due to restrictive action of the chest compression on the chest wall. An example chart showing a relationship between stroke volume (in milliliters (mL)) and depth of compression (in centimeters (cm)) is shown in FIG. 5. As shown in FIG. 5, the stroke volume increases a nonlinear function of compression depth, with the depth of compression having a lesser effect on stroke volume at very high compression depths.

It should be noted that the system 100, 200 of FIGS. 1 and 2 are advantageous over currently available systems because the system 100, 200 allows individuals to administer CPR using near-real-time feedback from the system 100, 200. By way of background, the current recommendation for CPR is to apply chest compression that are approximately five centimeters (~5 cm) deep. However, because of the variability of each individual, the 5 cm-deep compressions are not consistent or reliable. Unlike conventional CPR approaches, the system 100, 200 of FIGS. 1 and 2 permit an individual to apply chest compressions until the inspiration chamber pressure release valve 114 opens. If the individual administering CPR sees the opening of the inspiration chamber pressure release valve 114, then the individual knows immediately that sufficient force has been applied to the chest during CPR. In other words, rather than using an ill-defined metric of compression depth (e.g., ~5 cm), the system 100, 200 allows for a better-defined metric of chest compression, namely, the air (or $O_2$ or other gas) pressure that is applied to the lungs of the subject. In extreme cases, where the airway is obstructed, it is entirely possible for the inspiration chamber pressure release valve 114 to open because of the obstruction (rather than because of the pressure in the lungs). When a trained medical professional determines that the airway is obstructed (and thus prematurely opens the inspiration chamber pressure release valve 114), the professional can simply block the inspiration chamber pressure release valve 114 to permit even higher pressure in the inspiration chamber 102. Some embodiments contemplate transient pressures of up to ~300 $cmH_2O$ (if not higher). In some embodiments, pressures can range from approximately 30 $cmH_2O$ to approximately 300 $cmH_2O$.

Continuing, during decompression (or expansion) of the chambers 102, 122, the inspiration chamber 102 is filled with fresh gas (e.g., air, $O_2$, etc.) and expiration chamber 122 generates negative pressure in the airway. Negative intrathoracic pressure of the patient 310 in combination with the expansion of the chambers 102, 122 provides active extraction of the expired gas (e.g., $CO_2$) and results in deflation the lungs. It has been demonstrated that the generation of negative intrathoracic pressure during chest decompression while performing CPR may improve cardiac output by increasing heart filling volume.

The magnitude of pressure generated in inspiration chamber 102 during compression is controlled by the inspiration chamber pressure release valve 114, which can preferably be regulated from a positive pressure of approximately thirty (+30) to approximately three hundred (+300) $cmH_2O$. The magnitude of negative pressure generated by expiration chamber 122 during decompression is regulated by the expiration chamber pressure release valve 134, which can preferably be regulated from a negative pressure of approximately zero (~0, or atmospheric pressure) to approximately negative fifty (−50) cmH$_2$O.

The direction of airflow between inspiration chamber 102, the patient, and the expiration chamber 122 is regulated by the spring-loaded shuttle valve 140, which has a cracking pressure that is set to a value that is lower than a cracking pressure of the inspiration chamber pressure release valve 114.

The degree of compression of the chambers 102, 104 is regulated and limited, thereby providing an ability to adjust tidal volume generated by the inspiration chamber 102. By way of example, in adults the tidal volume ranges between approximately one hundred milliliters (~100 ml) and ~250 ml, while in children or infants the tidal volume is typically less than ~100 ml. The tidal volume of each breath is expected to be a little above, equal, or a little below physiological dead space, which in adult humans is from ~100 ml to ~150 ml, or from ~1.5 to ~2.0 ml per kilogram (kg) of body weight. At one hundred (100) compressions per minute, the system 100, 200 provides total minute ventilation of between ~10 liters (L) and ~25 L (mathematically, 100 breaths×100 ml or 100 breaths×250 ml). Due to active exhalation, the system 100, 200 can remove CO$_2$ using volumes that are smaller than the dead space by generating bi-directional laminar airflow within the airways (which is a likely mechanism for CO$_2$ removal in a high frequency oscillatory ventilator, which is known to operate with tidal volumes smaller than the physiologic dead space).

It is possible that lungs inflation using pressure equal to or greater than ~120 cmH$_2$O in synchrony with chest compressions can develop hyperventilation and respiratory alkalosis, which are known to reduce cerebral blood flow. This condition can be compensated by an admixture of approximately three percent (~3%) CO$_2$ to the gas used for ventilation (e.g., O$_2$+3% CO$_2$, air+3% CO$_2$, etc.). For other embodiments, the admixture is between ~3% CO$_2$ and ~5% CO$_2$.

The dual chambers 102, 122 are intended to work in synchrony with chest compression CPR, which can be performed either manually or with CPR devices such as the Zoll ResQPUMP, Zoll AutoPulse, Stryker Lucas 3 Chest Compression System, etc.

As an alternative, it should be appreciated that the breaths administered using the system 100, 200 can be administered manually by a dedicated rescuer, while synchronization of the breaths with chest compression is done by observing another rescuer performing chest compressions. Also, the breaths using the system 100, 200 can be administered mechanically using piston or solenoid-driven compressions and decompressions of the chambers. Also, the breaths can be synchronized by using either chest skin impedance electrodes or by ECG electrodes, by detecting heart compressions electrical artifacts, by pulse oximeter, or by any other pulse wave measuring device (e.g., doppler, etc.). Any commercially available contemporary mechanical ventilator can be converted to be capable of delivering a CCSBV mode of ventilation by modification of the device to implement functions and features as set out herein, including for example, adding negative pressure to an exhalation part of the circuit to generate active lung deflation triggered by the chest decompression. A ventilator equipped with CCSBV mode can be used for patients with congestive heart failure with spontaneously contracting hearts, by using either ECG or a pacemaker as a trigger to initiate a breath.

Positive pressure artificial inhalation at a fast rate has an ability to produce elevation of intrathoracic pressure, which would be applied to all surfaces of the heart. Synchronization of positive pressure inhalations with chest compressions can reduce the loss of compression force by simultaneously pressing on the heart from other directions, thereby increasing stroke volume, blood pressure, and cardiac output. During the decompression phase of CPR, the heart is passively filled with blood, depending on the degree of relaxation of the myocardium and the magnitude of the pressure gradient between the venous pressure and intrathoracic pressure. Synchronization of the chest decompression and negative pressure generated by the system 100, 200 during exhalation can improve venous return to the heart by generating higher pressure gradients between the venous circulation and the heart, thereby improving filling of the heart chambers with venous blood. This, in turn, results in more effective expulsion of blood from the heart, thereby improving CPR outcomes.

Although exemplary embodiments have been shown and described, it will be clear to those of ordinary skill in the art that a number of changes, modifications, or alterations to the disclosure as described may be made. For example, the inspiration chamber 102 and the expiration chamber 122 can be implemented using bellows, plungers, or other known mechanical means. Furthermore, although compressible springs 192, 194 are shown to be contained inside of the inspiration chamber 102 and the expiration chamber 122, it should be appreciated that, for some embodiments, the location of the compressible springs 192, 194 is outside of the chambers 102, 122. Moreover, while mechanical valves (such as shuttle valves) are shown in various embodiments, it should be appreciated that alternative embodiments can use electromechanical valves in lieu of the mechanical valves or in addition to the mechanical valves. All such changes, modifications, and alterations should therefore be seen as within the scope of the disclosure.

What is claimed is:

1. A system comprising:
    an inspiration chamber having an inspiration chamber top and an inspiration chamber bottom;
    an inspiration chamber inlet for receiving gas into the inspiration chamber;
    an inspiration chamber outlet for expelling the gas from the inspiration chamber at a pressure of between one-hundred-and-twenty centimeters of water (120 cmH$_2$O) and three-hundred centimeters of water (300 cmH$_2$O);
    an expiration chamber having an expiration chamber top and an expiration chamber bottom, the expiration chamber top aligning with the inspiration chamber top, the expiration chamber bottom aligning with the inspiration chamber bottom;
    an expiration chamber inlet for receiving expired gas at a pressure of between negative fifty centimeters of water (−50 cmH$_2$O) and zero centimeters of water (0 cmH$_2$O);
    an expiration chamber outlet for expelling the expired gas;
    a subject conduit for receiving the gas from the inspiration chamber and providing the gas to a subject at a pressure of between 120 cmH$_2$O and 300 cmH$_2$O, the subject conduit further for receiving the expired gas from the subject at a pressure of between −50 cmH$_2$O and 0 cmH$_2$O and providing the expired gas to the expiration chamber;
    a valve operatively coupled to the inspiration chamber outlet, the valve further being operatively coupled to the expiration chamber inlet, the valve for selectively opening the inspiration chamber outlet and closing the expiration chamber inlet when positive pressure from the inspiration chamber is applied to the valve, the valve further for selectively closing the inspiration chamber outlet and opening the expiration chamber inlet when no positive pressure is applied to the valve from the inspiration chamber; wherein: the inspiration chamber comprises an inspiration chamber pressure release valve for opening when the pressure in the inspiration chamber is higher than a predefined threshold maximum positive pressure; the gas in the inspiration chamber is at a temperature that is sufficient to induce therapeutic hypothermia; the predefined threshold maximum positive pressure higher than 300 centimeters of water (300 cmH$_2$O); and the expiration chamber comprises an expiration chamber pressure release valve for opening when the pressure in the expiration chamber is lower than −50 cm H$_2$O.

2. The system of claim 1, wherein:
the inspiration chamber is selectively compressible and expandable; and
the inspiration chamber inlet receives the gas when pressure in the inspiration chamber is lower than a first predefined threshold pressure.

3. The system of claim 2, wherein the first predefined threshold pressure is atmospheric pressure.

4. The system of claim 3, wherein:
the inspiration chamber comprises an inspiration chamber inlet valve operatively coupled to the inspiration chamber inlet; and
the inspiration chamber inlet valve is configured to open when pressure in the inspiration chamber is lower than the first predefined threshold pressure.

5. The system of claim 4, wherein:
the inspiration chamber inlet valve is configured to close when the pressure in the inspiration chamber is higher than a second predefined threshold pressure; and
the second predefined threshold pressure is atmospheric pressure.

6. The system of claim 1, wherein:
the expiration chamber outlet expels the expired gas when pressure in the expiration chamber is higher than a predefined threshold pressure;
the expiration chamber comprises an expiration chamber outlet valve operatively coupled to the expiration chamber outlet;
the expiration chamber outlet valve is configured to open when the pressure in the expiration chamber is higher than the predefined threshold pressure;
the expiration chamber outlet valve is configured to close when pressure in the expiration chamber is lower than the predefined threshold pressure; and
the expiration chamber inlet receives the expired gas when pressure in the expiration chamber is lower than a different predefined threshold pressure.

7. The system of claim 1, further comprising:
a rigid top mechanically coupled to the inspiration chamber top, the rigid top further being mechanically coupled to the expiration chamber top; and
a rigid bottom mechanically coupled to the inspiration chamber bottom, the rigid bottom further being mechanically coupled to the expiration chamber bottom, the rigid bottom in cooperation with the rigid top for concurrently compressing both the inspiration chamber and the expiration chamber.

8. The system of claim 7, further comprising:
expanding means for concurrently expanding both the inspiration chamber and the expiration chamber after the inspiration chamber and the expiration chamber are compressed, the expanding means further for expanding both the inspiration chamber and the expiration chamber to its pre-compression state within a predefined rebound time.

9. The system of claim 8, wherein the predefined rebound time is three hundred milliseconds (300 ms).

10. The system of claim 8, wherein the expanding means comprises a deformable wall located between the rigid top and the rigid bottom, the deformable wall having a default shape prior to compression of the inspiration chamber and the expiration chamber, the deformable wall further having a predefined stiffness, the deformable wall for deforming concurrently with the compression of the inspiration chamber and the expiration chamber, the deformable wall further for returning to its default shape within the predefined rebound time.

11. The system of claim 8, wherein the expanding means comprises a compressible spring located between the rigid top and the rigid bottom, the compressible spring having a spring constant, the spring for compressing concurrently with the compression of the inspiration chamber and the expiration chamber, the spring further for returning to its pre-compression load within the predefined rebound time after being compressed.

12. The system of claim 7, further comprising handles located on the rigid top.

13. The system of claim 7, wherein the rigid bottom is further for applying pressure to a sternum of the subject during cardiopulmonary resuscitation (CPR).

14. The system of claim 1, wherein the valve is a spring-loaded shuttle valve comprising:
an inspiration conduit mechanically coupled to the inspiration chamber outlet;
an expiration conduit mechanically coupled to the expiration chamber inlet;
the subject conduit being located between the inspiration conduit and the expiration conduit, the subject conduit for receiving the gas from the inspiration chamber and providing the gas to the subject, the subject conduit further for receiving the expired gas from the subject and providing the expired gas to the expiration chamber; and
a spring-loaded shuttle having a default position that closes the inspiration conduit and opens the expiration conduit in the absence of pressure being applied to the spring-loaded shuttle, the spring-loaded shuttle for selectively opening the inspiration conduit and closing the expiration conduit when positive pressure from the inspiration chamber is applied to the spring-loaded shuttle, the spring-loaded shuttle further for selectively closing the inspiration conduit and opening the expiration conduit when no positive pressure is applied from the inspiration chamber to the spring-loaded shuttle.

15. A process for administering cardiopulmonary resuscitation (CPR) using the system of claim 1, the process comprising:
providing the gas to an airway of the subject at a positive pressure of between 120 cmH$_2$O and 300 cmH$_2$O;
compressing a chest of the subject synchronously with the providing of the gas;
drawing the expired gas from the airway of the subject at a negative pressure of between 0 cmH$_2$O and −50 cmH$_2$O; and allowing decompression of the chest synchronously with the drawing of the expired gas.

* * * * *